United States Patent [19]
Wadsworth et al.

[11] Patent Number: 5,720,936
[45] Date of Patent: Feb. 24, 1998

[54] TRANSGENIC MOUSE ASSAY FOR COMPOUNDS AFFECTING AMYLOID PROTEIN PROCESSING

[75] Inventors: Samuel Wadsworth, Shrewsbury; Benjamin Snyder, Worcester; Cha-Mer Wei, Framingham; Paul J. Leibowitz, Brookline, all of Mass.

[73] Assignee: Athena Neurosciences, Inc., South San Francisco, Calif.

[21] Appl. No.: 282,227

[22] Filed: Jul. 29, 1994

Related U.S. Application Data

[63] Continuation of Ser. No. 915,469, Jul. 16, 1992, abandoned, which is a continuation-in-part of Ser. No. 817,584, Jan. 7, 1992, abandoned.

[51] Int. Cl.$^6$ ............... A61K 49/00; C12N 5/00; C12N 15/00
[52] U.S. Cl. ............ 424/9.1; 800/2; 800/DIG. 1; 935/60; 935/62
[58] Field of Search ............... 800/2, DIG. 1; 424/9, 9.1; 935/60, 62

[56] References Cited

U.S. PATENT DOCUMENTS 5,387,742  2/1995  Cordell.

FOREIGN PATENT DOCUMENTS

| | | |
|---|---|---|
| 0 451 700 AT WO A1 | 12/1991 | European Pat. Off. |
| 8906689 WO A | 7/1989 | WIPO. |
| 9206187 WO A | 4/1992 | WIPO. |
| 9213069 WO A1 | 8/1992 | WIPO. |
| 9302189 | 2/1993 | WIPO. |
| US91/04447 | 12/1993 | WIPO. |

OTHER PUBLICATIONS

Games et al (1995) Nature 373, 523–527.
Duff et al (1995) Nature 373, 476–477.
Genetic Eng. News, Mar. 1, 1995, pp. 1,3 & 31.
Seehoe (1991) Nature 354, 432–433.
Burke et al (1987) Science 236, 806–812.
Mansour et al (1988) nature 336, 348–352.
Scangos et al (1987) Advin Gentics, 285–322.
Kang et al (1987) Nature 325, 733–736.
Ponte et al (1988) Nature 331, 929–927.
Kitaguchi et al (1988) Nature 331, 530–532.
Goate et al (1991) Nature 349, 704–706.
Salbaum et al (1988) EMBO J. 7, 2807–2813.
Sakimura et al (1987) Gene 60, 103–113.
Swanson et al (1985) Nature 317, 363–366.
Sakimura, K., et al., "Partial Purification and Characterization of Messenger RNA Coding 14–3–2 Protein from Rat Brain," *Journal of Neurochemistry* 39(2):366–370 (1982).
Sakimura, K., et al., "The structure and expression of neuron–specific enolase gene," *Gene* 60, 103–113 (1987).

Salbaum, et al., "The promoter of Alzheimer's disease amyloid A4 precursor gene," *EMBO J.* 7, 2807–2813 (1988).
Sandhu, F., et al., "Expression of the Human β–Amyloid Protein of Alzheimer's Disease Specifically in the Brains of Transgenic Mice," *The Journal of Biological Chemistry* 266(32): 21331–21334 (Nov. 15, 1991).
Scangos, et al., "Gene Transfer into mice," *Adv. in Genet.* 24, 285–322 (1987).
Selkoe, D., "Amyloid Protein and Alzheimer's Disease," *Scientific American* 265(5):68–76 (Nov. 1991).
Selkoe, D., "In the Beginning . . ." *Nature* 354:432–433 (Dec. 12, 1991).
Spencer, D., et al., "Behavioral Impairments Related to Cognitive Dysfunction in the Autoimmune New Zealand Black Mouse," *Behavioral Neuroscience* 100(3):353–358 (1986).
St. George–Hyslop, P., et al., "The Genetic Defect Causig Familial Alzheimer's Disease Maps on Chromosome 21," *Science* 235:885–890 (Feb. 20, 1987).
St. George–Hyslop, P., et al., "Absence of Duplication of Chromosome 21 Genes in Familial and Sporadic Alzheimer's Disease," *Science* 238:664–666 (Oct. 30, 1987).
Swanson, et al., "Novel developmental specificity in the nervous system of transgenic animals expressing growth hormone fusion genes," *Nature* 317, 363–366 (1985).

(List continued on next page.)

*Primary Examiner*—Deborah Crouch
*Attorney, Agent, or Firm*—Arnall Golden & Gregory, LLP

[57] ABSTRACT

The construction of transgenic animal models for testing potential treatments for Alzheimer's disease are described. The models are characterized by a greater similarity to the conditions existing in naturally occurring Alzheimer's disease, based on expression of all three forms of the β–amyloid precursor protein (APP), $APP_{695}$, $APP_{751}$, and $APP_{770}$), as well as various point mutations based on naturally occurring mutations, such as the London and Indiana familial Alzheimer's disease (FAD) mutations at amino acid 717, and predicted mutations in the APP gene. The APP gene constructs are prepared using the naturally occurring promoter, as well as inducible promoters such as the mouse metallothionine promoter, which can be regulated by addition of heavy metals such as zinc to the animal's water or diet, and promoters such as the rat neuron specific enolase promoter, human β actin gene promoter, human platelet derived growth factor B (PDGF-B) chain gene promoter, rat sodium channel gene promoter, mouse myelin basic protein gene promoter, human copper-zinc superoxide dismutase gene promoter, and mammalian POU-domain regulatory gene promoter. The constructs are introduced into animal embryos using standard techniques such as microinjection. Animal cells can be isolated from the transgenic animals or prepared using the same constructs with standard techniques such as lipofection or electroporation. The transgenic animals, or animal cells, are used to screen for compounds altering the pathological course of Alzheimer's Disease as measured by their effect on the amount and histopathology of APP and β–amyloid peptide in the animals, as well as by behavioral alterations.

6 Claims, 3 Drawing Sheets

OTHER PUBLICATIONS

Tanzi, R., et al., "Amyloid β Protein Gene: cDNA, mRNA Distribution and Genetic Linkage Near the Alzheimer Locus," *Science* 235:881–884 (Feb. 20, 1987).

Tanzi, R., et al., "The Genetic Defect in Familial Alzheimer's Disease is not Tightly Linked to the Amyloid β–Protein Gene," *Nature* 329:156–157 (Sep. 10, 1987).

Tanzi, R., et al., "Molecular Genetic Approaches to Alzheimer's Disease," *Trends in Neuroscience* 12(4):152–158 (1989).

Tanzi, R., et al., "Protease Inhibitor Domain Encoded by an Amyloid Protein Precursor mRNA Associated with Alzheimer's Disease," *Nature* 331:528–530 (Feb. 11, 1988).

Tanzi,R., et al., "The Amyloid β Protein Gene is not Duplicated in Brains from Patients with Alzheimer's Disease," *Science* 238:666–669 (Oct. 30, 1987).

Tate–Ostroff, B., et al., "Identification of Cellular and Extracellular Sites of Amyloid Precursor Protein Extracytoplasmic Domain in Normal and Alzheimer Disease Brains," *Proceedings of the National Academy of Science (U.S.A.)* 86:745–749 (Jan. 1989).

Van Broeckhoven, C., et al., "Amyloid β Protein Precursor Gene and Hereditary Cerebral Hemorrhage with Amyloidosis (Dutch)," *Science* 248:1120–1122 (Jun. 1990).

Weidemann, A., et al., "Identification, Biogenesis, and Localization of Precursors of Alzheimer's Disease A4 Amyloid Protein," *Cell* 57:115–126 (Apr. 7, 1989).

Wirak, D., et al., "Deposits of Amyloid β Protein in the Central Nervous System of Transgenic Mice," *Science* 253:323–325 (Jul. 19, 1991).

Wirak, D., et al., "Regulatory Region of Human Amyloid Precursor Protein (APP) Gene Promotes Neuron–Specific Gene Expression in the CNS of Transgenic Mice," *European Molecular Biology Organization Journal* 10(2):289–296 (1991).

Yamaguchi et al., "Transgenic mice for the amyloid precursor protein 695 isoform have impaired spatial memory," *NeuroReport* 2:781–784 (Dec. 12, 1991).

Yamamoto, M., et al., "Effects of Indeloxazine Hydrochloride on Cognitive Disturbance in Cycloheximide–Treated Mice," *Journal of Pharmacy and Pharmacology* 41:284–286 (1989).

Yoshikai, et al., "Genomic Organization of the Human Amyloid Beta–Protein Precursor Gene," *Gene:*257–263 (1990).

Maruyama, K., et al., "Formation of Amyloid–Like Fibrils in COS Cells Overexpressing Part of the Alzheimer Amyloid Protein Precursor," *Nature* 347:566–569 (Oct. 11, 1990).

Marx, J., "Mutation Identified as a Possible Cause of Alzheimer's Disease," *Science* 251:876–877 (Feb. 22, 1991).

Marx, J., "Alzheimer's Research Moves to Mice," *Science* 253:266–267 (Jul. 19, 1991).

Masters, C., et al., "Amyloid Plaque Core Protein in Alzheimer Disease and Down Syndrome," *Proceedings of the National Academy of Science (U.S.A.)* 82:4245–4249 (Jun. 1985).

Murrell, J., et al., "A Mutation in the Amyloid Precursor Protein Associated with Hereditary Alzheimer's Disease," *Science* 254:97–99 (Oct. 4, 1991).

Patterson, D., et al., "Mapping of the Gene Encoding the β–Amyloid Precursor Protein and its Relationship to the Down Syndrome Region of Chromosome 21," *Proceedings of the National Academy of Science (U.S.A.)* 85:8266–8270 (Nov. 1988).

Pericak–Vance, M., et al., "Genetic Linkage Studies in Alzheimer's Disease Families," *Experimental Neurology* 102:271–279 (1988).

Podlisny, M., et al., "Gene Dosage of the Amyloid β Precursor Protein in Alzheimer's Disease," *Science* 238:669–671 (Oct. 30, 1987).

Ponte, P., et al., "A New A4 Amyloid mRNA Contains a Domain Homologous to Serine Proteinase Inhibitors," *Nature* 331:525–527 (Feb. 11, 1988).

Price, D., et al., "Cellular and Molecular Biology of Alzheimer's Disease," *BioAssays* 10(2&3):69–74 (Feb.–Mar. 1989).

Price, D., et al., "Alzheimer's Disease and Down's Syndrome," *Annals of the New York Academy of Sciences:*145–164 (1982).

Quon, D., et al., "Formation of β–Amyloid Protein Deposits in Brains of Transgenic Mice," *Nature* 352:239–241 (Jul. 18, 1991).

Reddy, V., et al., "The Genome of Simian Virus 40," *Science* 200:494–502 (May 5, 1978).

Robakis, N., et al., "Molecular Cloning and Characterization of a cDNA Encoding the Cerebrovascular and the Neuritic Plaque Amyloid Peptides," *Proceedings of the National Academy of Science (U.S.A.)* 84:4190–4194 (Jun. 1987).

Saitoh, T., et al., "Secreted Form of Amyloid β Protein Precursor is Involved in the Growth Regulation of Fibroblasts," *Cell* 58:615–622 (Aug. 25, 1989).

Joachim, C., et al., "Amyloid β–Protein Deposition in Tissues Other than Brain in Alzheimer's Disease," *Nature* 341:226–230 (Sep. 21, 1989).

Kang, J., et al., "The Precursor of Alzheimer's Disease Amyloid A4 Protein Resembles a Cell–Surface Receptor," *Nature* 325:733–736 (Feb. 19, 1987).

Katzman, R., "Alzheimer's Disease," *The New England Journal of Medicine* 314(15):964–973 (Apr. 10, 1986).

Kawabata, S., et al., "Amyloid Plaques, Neurofibrillary Tangles and Neuronal Loss in Brains of Transgenic Mice Overexpressing a C–Terminal Fragment of Human Amyloid Precursor Protein," *Nature* 354:476–478 (Dec. 12, 1991).

Kidd, M., "Paired Helical Filaments in Electron Microscopy of Alzheimer's Disease," *Nature* 197:192–193 (Jan. 12, 1963).

Kitaguchi, N., et al., "Novel Precursor of Alzheimer's Disease Amyloid Protein Shows Protease Inhibitory Activity," *Nature* 331:530–532 (Feb. 11, 1988).

Kowall, N., et al., "An In Vivo Model for the Neurodegenerative Effects of β Amyloid and Protection by Substance P," *Proceedings of the National Academy of Science (U.S.A.)* 88:7247–7251 (Aug. 1991).

Lee, V., "Unraveling the Mystery of the Paired Helical Filaments of Alzheimer's Disease," *the Journal of NIH Research* 3:52–55 (Nov. 1991).

Lemaire, H., et al., "The PreA4$_{695}$ Precursor Protein of Alzheimer's Disease A4 Amyloid is Encoded by 16 Exons," *Nucleic Acids Research* 17(2):517–522 (1989).

Levy, E., et al., "Mutation of the Alzheimer's Di8sease Amyloid Gene in Hereditary Cerebral Hemorrhage, Dutch Type," *Science* 248:1124–1126 (Jun. 1990).

Maiocha, R., et al., "Monoclonal Antibody to Embryonic CNS Antigen A2B5 Provides Evidence for the Involvement of Membrane Components at Sites of Alzheimer Degeneration and Detects Sulfatides as Well as Gangliosides," *Journal of Neurochemistry* 53(3):953–961 (1989).

Maiocha, R., et al., "Immunostaining of Neurofilament Protein in Human Postmortem Cortex: A Sensitive and Specific Approach to the Pattern Analysis of Human Cortical Cytoarchitecture," *Canadian Journal of Biochemistry and Cell Biology* 63:577–584 (1985).

Manning, R., et al., "Identification in Rodents and other Species of an mRNA Homologous to the Human β–Amyloid Precursor," *Molecular Brain Research* 3:293–298 (1988).

Marotta, C., et al., "Overexpression of Amyloid Precursor Protein A4 (β–Amyloid) Immunoreactivity in Genetically Transformed Cells: Implications for a Cellular Model of Alzheimer Amyloidosis," *Proceedings of the National Academy of Science (U.S.A.)* 86:337–341 (Jan. 1989).

Martin, L.m et al., "Amyloid Presursor Protein in Aged Nonhuman Primates," *Proceedings of the National Academy of Science (U.S.A.)* 88:1461–1465 (Feb. 1991).

Chou, W., et al., "Alzheimer Cortical Neurons Containing Abundant Amyloid mRNA. Relationship to Amyloid Deposition and Senile Plaques," *Journal Psychiatric Research* 24(1):37–50 (1990).

David, F., et al., "Absence of a Close Linkage Between Alzheimer's Disease Susceptibility Gene and a Polymorphic DNA Probe Coding for β–Amyloid," *Biomedicine & Pharmacotherapy* 42:575–578 (1988).

Davies, P., "Alz–50, A68, and the Paired Helical Filaments of Alzheimer's Disease," *The Journal of NIH Research* 3:53–56 (Nov. 1991).

DeFeudis, F., "Beta–Amyloid Protein in Transgenic Mice," *Drug News & Perspectives* 4(10):617–619 (Dec. 1991).

Delabar, J., et al., "β Amyloid Gene Duplication in Alzheimer's Disease and Karyotypically Normal Down Syndrome," *Science* 235:1390–1392 (Mar. 13, 1987).

Flood, J., et al., "Amnestic Effects in Mice of Four Synthetic Peptides Homologous to Amyloid β Protein from Patients with Alzheimer Disease," *Proceedings of the National Acaemy of Science (U.S.A.)* 88:3363–3366 (Apr. 1991).

Furuya, H., et al., "Amyloid β–Protein Gene Duplication is not Common in Alzheimer's Disease: Analysis by Polymorphic Restriction Fragments," *Biochemical and Biophysical Research Communications* 150(1):75–81 (Jan. 15, 1988).

Garfield, J., et al., "Differential Effects of Ketamine Stereoisomers on Maze Performance in the Mouse," *Anesthesiology* 63:681–683 (1985).

Glanville, N., et al., "Structure of Mouse Metallothionein–I Gene and its mRNA," *Nature* 292:267–269 (Jul. 6, 1981).

Glenner, G., et al., "Alzheimer's Disease: Initial Report of the Purification and Characterization of a Novel Cerebrovascular Amyloid Protein," *Biochemical and Biophysical Research Communications* 120(3):885–890 (May 16, 1984).

Goate, A., et al., "Segregation of a Missense Mutation in the Amyloid Precursor Protein Gene with Familial Alzheimer's Disease," *Nature* 349:704–706 (Feb. 2, 1991).

Golde, T., et al., "Expression of β Amyloid Protein Precursor mRNAs: Recognition of a Novel Alternatively Spliced Form and Quantitation in Alzheimer's Disease Using PCR," *Neuron* 4:253–267 (Feb. 1990).

Goldgaber, D., et al., "Characterization and Chromosomal Localization of a cDNA Encoding Brain Amyloid of Alzheimer's Disease," *Science* 235:877–880 (Feb. 20, 1987).

Hammer, R., et al., "Spontaneous Inflammatory Disease in Transgenic Rats Expressing HLA–B27 and Human $β_2$m: An Animal Model of HLA–B27–Associated Human Disorders," *Cell* 63:1099–1112 (Nov. 30, 1990).

Jenkins, E., et al., "Fine Mapping of an Alzheimer Disease–Associated Gene Encoding Beta–Amyloid Protein," *Biochemical and Biophysical Research Communications* 151(1):1–8 (Feb. 29, 1988).

Hyman, et al., "Amyloid, demintia and Alzheimer's disease" *Current Opinion in Neurology and Neurosurgery,* 1992, 5:88–93.

Argyle, N., et al., "Psychogeriatric Patients: Their Supporters' Problems," *Age and Ageing* 14:355–360 (1985).

Brown, B., et al., "Axonal Polypeptides Cross–Reactive with Antibodies to Neurofilament Proteins," Journal of Neurochemistry 40(2):299–308 (1983).

Chartier–Harlin, M., et al., "Early–Onset Alzheimer's Disease Caused by Mutations at Codon 717 of the β–Amyloid Precursor Protein Gene," *Nature* 353:844–846 (Oct. 31, 1991).

Podlisny et al (1992) Neurobiol. Aging 13, 561–567.

Mullins et al (1993) Hypertension 22, 630–633.

Marx et al (1992) Science 255, 1200–1202.

Felsenstein et al (1995) Alzheimer's and Parkinson's Diseases, ed. I. Hanin et al, Plenum Press, NY, pp. 401–409.

Lannfelt et al (1993) Behav. Brain Res. 57, 207–213.

Joachim et al (1992) Alzheimer Disease and Associated Disorders 6, 7–34.

Meena–Leist et al (1993) Ann. Clin. Lab. Sci. 23, 173–177.

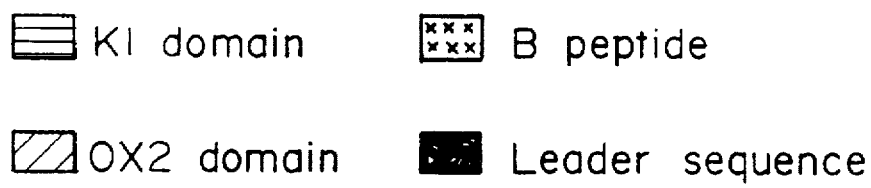
FIG. 1a
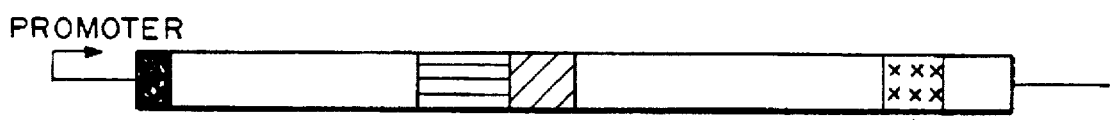
FIG. 1b
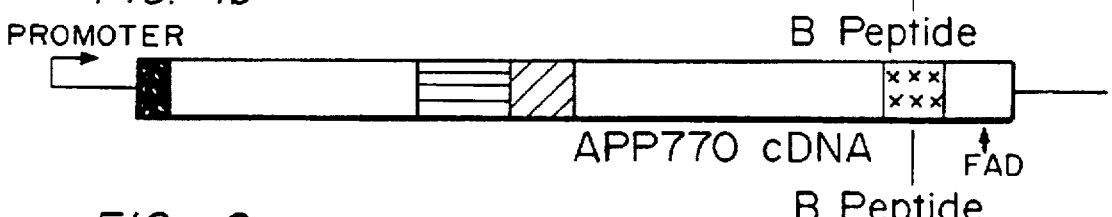
FIG. 2a
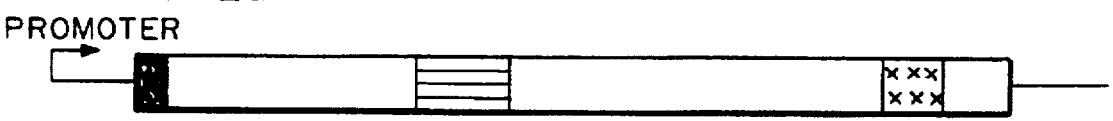
FIG. 2b
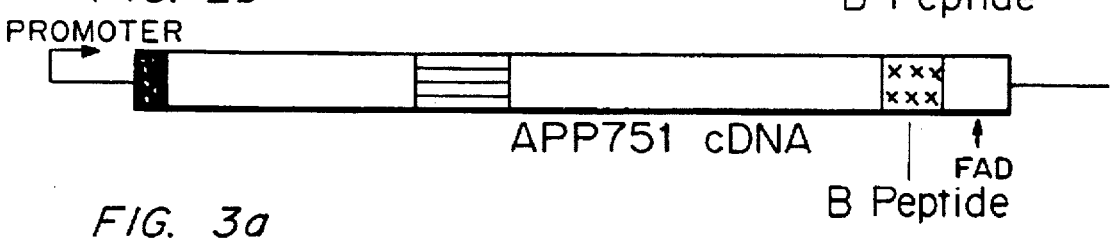
FIG. 3a
FIG. 3b
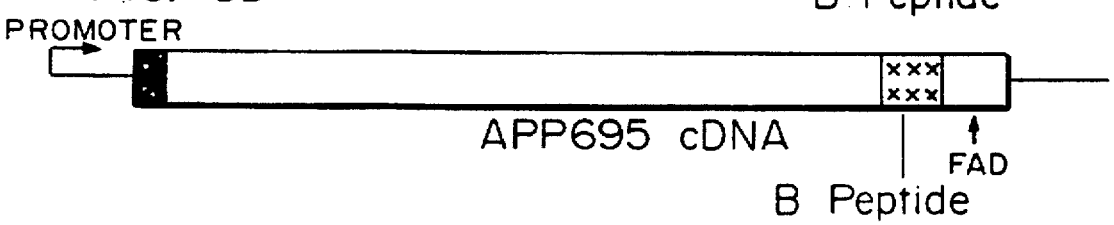

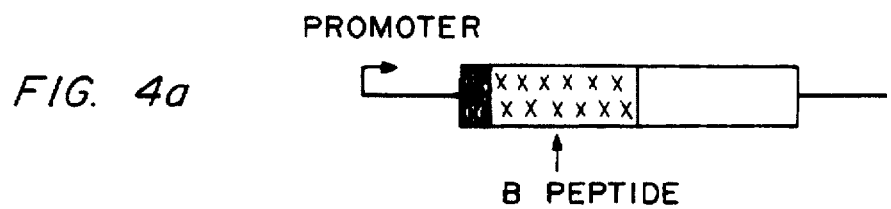
FIG. 4a
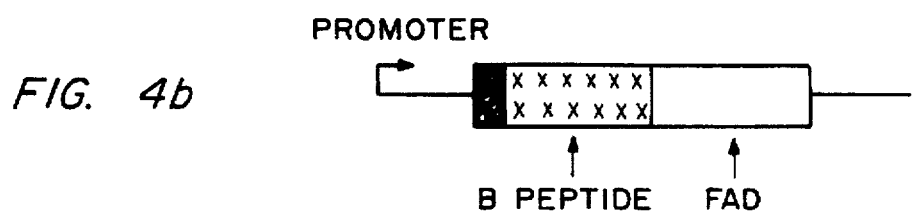
FIG. 4b
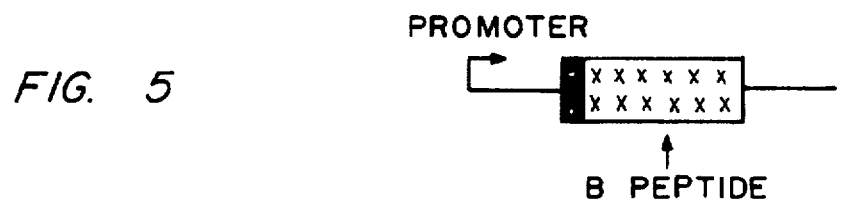
FIG. 5
FIG. 6a
FIG. 6b
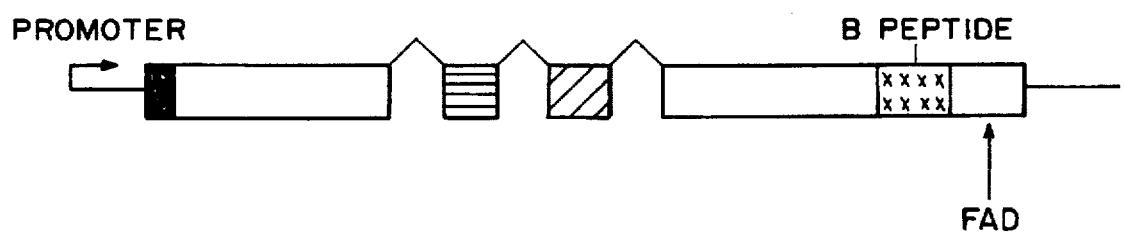

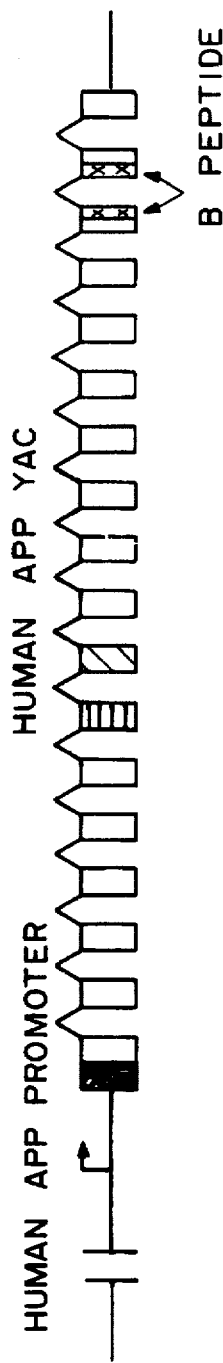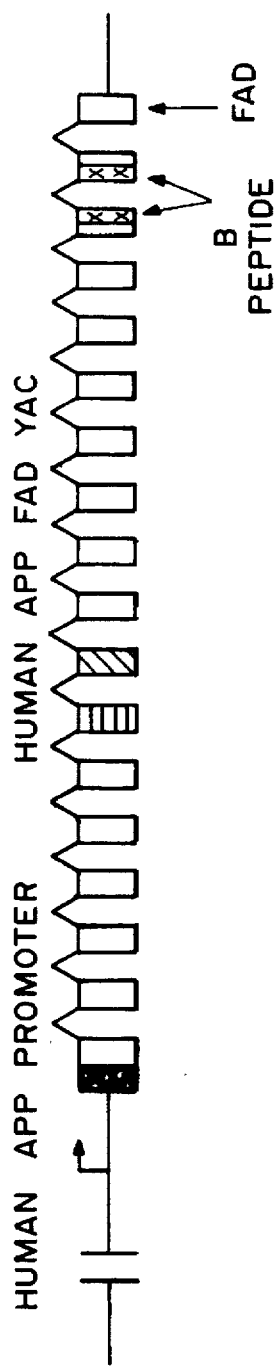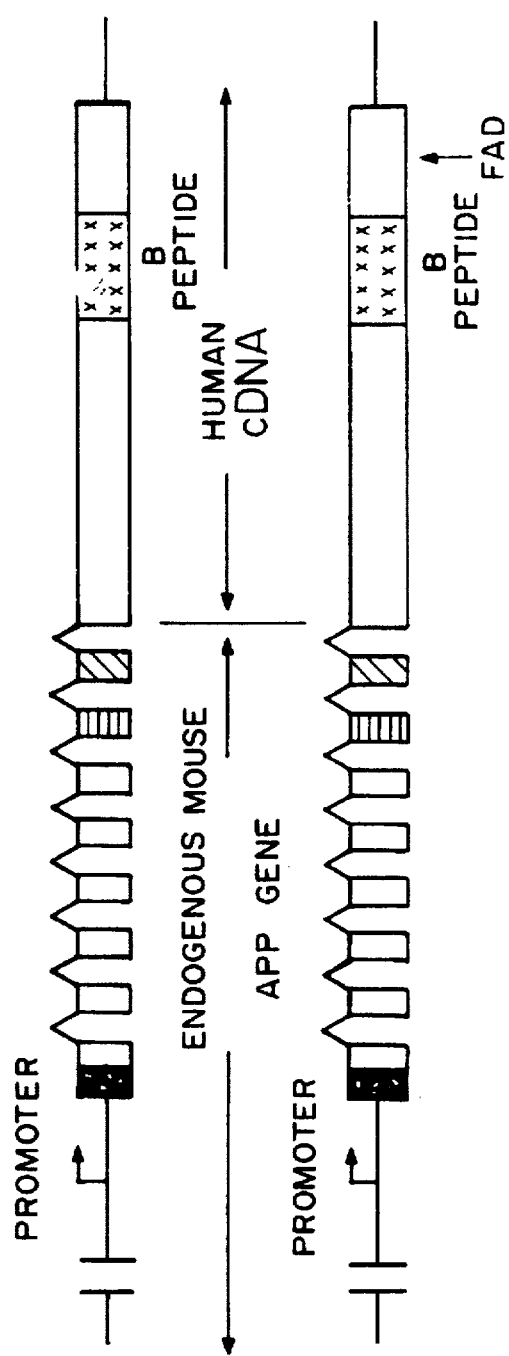
FIG. 7a
FIG. 7b
FIG. 8

TRANSGENIC MOUSE ASSAY FOR COMPOUNDS AFFECTING AMYLOID PROTEIN PROCESSING

BACKGROUND OF THE INVENTION

This is a continuation of U.S. Ser. No. 07/915,469 filed Jul. 16, 1992, now abandoned, which is a continuation-in-part of U.S. patent application Ser. No. 07/817,584, filed Jan. 7, 1992, now abandoned, entitled Transgenic Animal Models for Alzheimer's Disease, by Samuel Wadsworth, Benjamin Snyder, Vermuri B. Reddy, and Cha-mer Wei.

Transgenic technology is described for the production of animals that exhibit symptoms of human Alzheimer's disease through the expression of the Alzheimer's precursor protein or a modified version thereof.

Alzheimer's Disease (AD) is a degenerative disorder of the brain first described by Alios Alzheimer in 1907 after examining one of his patients who suffered drastic reduction in cognitive abilities and had generalized dementia ("The early story of Alzheimer's Disease", edited by Bick K, Amaducci L, and Pepeu G. (Raven Press, New York 1987). It is the leading cause of dementia in elderly persons. AD patients have increased problems with memory loss and intellectual functions which progress to the point where they cannot function as normal individuals. With the loss of intellectual skills the patients exhibit personality changes, socially inappropriate actions and schizophrenia ("A guide to the understanding of Alzheimer's Disease and related disorders", edited by Jorm AF.; (New York University Press, New York 1987). AD is devastating for both victims and their families, for there is no effective palliative or preventive treatment for the inevitable neurodegeneration. The most common problems in the Alzheimer's patient are inability to dress unaided, restlessness by day, urinary incontinence and sleep disturbances. The family members report embarrassment, anxiety, depression, and a decreased social life.

The impact of AD on society and on the national economy is enormous. It is expected that the demented elderly population in the United States will increase by 41% by the year 2000. It is expensive for the health care systems that must provide institutional and ancillary care for the patients at an estimated annual cost of $40 billion (Jorm, 1987; Fisher, LM: New York Times, Aug. 23, 1989 D1 "Alzheimer's Disease", edited by Reisberg, B.; (The Free Press, New York & London 1983). These factors imply preventive action must be taken to decrease AD incidence by allocating resources into AD research.

At a macroscopic level, the brains of AD patients are usually smaller, sometimes weighing less than 1,000 grams. At a microscopic level, the histopathological symptoms of AD include neurofibrillary tangles (NFT), neuritic plagues, and degeneration of neurons. AD patients exhibit degeneration of nerve cells in the frontal and temporal cortex of the cerebral cortex, pyramidal neurons of hippocampus, neurons in the medial, medial central, and cortical nuclei of the amygdala, noradrenergic neurons in the locus coeruleus, and the neurons in the basal forebrain cholinergic system. Loss of neurons in the cholinergic system leads to a consistent deficit in cholinergic presynaptic markers in AD (Reisberg, 1983; "Alzheimer's Disease and related disorders, research and development" edited by Kelly WE; (Charles C. Thomas, Springfield, Ill. 1984).

AD is associated with neuritic plaques measuring up to 200 μm in diameter in the cortex, hippocampus, subiculum, hippocampal gyrus, and amygdala. One of the principal constituents of neuritic plaques is amyloid, which is stained bycongo red (Reisberg, 1983; Kelly, 1984). Amyloid plaques are extracellular, pink—or rust—colored in bright field, and birefringent in polarized light. The plagues are composed of polypeptide fibrils and are often present around blood vessels, reducing blood supply to various neurons in the brain.

Various factors such as genetic predisposition, infectious agents, toxins, metals, and head trauma have all been suggested as possible mechanisms of AD neuropathy. However, available evidence strongly indicates two distinct types of genetic predisposition for AD. First, molecular analysis has provided evidence for mutations in the amyloid precursor protein (APP) gene in certain AD-stricken families (Goate, et al. *Nature* 349:704–706 (1991); Murrell, J, et al. *Science* 254; 97–99, 1991; Chartier-Harlin, M-C, et al. *Nature* 353, 844–846 (1991)). Second, in certain other families with a clear genetic predisposition to AD, the mutation maps to chromosome 21 but is distinct from the APP locus (Tanzi, R. E., et al. *Nature*, 331;528–530 (1988)).

Amyloid plaques are abundantly present in AD patients and in Down's Syndrome individuals surviving to the age of 40. The plaques are also present in the normal aging brain, although at a lower number. These plaques are made up of the amyloid β peptide (β peptide) (Glenner and Wong, et al., *Biochem. Biophys. Res. Comm.* 120:885–890 (1984)), which is also the main protein constituent in cerebrovascular deposits and neurofibrillary tangles. The peptide is a filamentous material that is arranged in beta-pleated sheets and has a molecular weight of 4.2–4.5 kd. It is a hydrophobic peptide comprising 39–42 amino acids. The determination of its amino acid sequence led to the cloning of the APP cDNA (Kang, et al., *Nature* 325:733–735 (1987); Goldgaber, et al., *Science* 235:877–880 (1987); Robakis et al., *Proc. Natl. Acad. Sci.* 84:4190–4194 (1987); Tanzi, et al., *Nature* 331:528–530 (1988) and genomic APP DNA (Lemaire et al., *Nucl. Acids Res.* 17:517–522 (1989); Yoshikai, et al., *Gene* 87, 257–263 (1990). Three forms of APP cDNAs (APP695, APP751, and APP770) have been isolated, and arise from a single precursor RNA by alternate splicing. The gene spans more than 175 Kb with 18 exons (Yoshikai, et al., 1990). APP contains three extracellular domains, a transmembrane region and a cytoplasmic domain. The B peptide consists of 28 amino acids just outside the membrane and 14 residues of the hydrophobic transmembrane domain. Thus, the β peptide is a cleavage product of APP normally found in brain and other tissues such as heart, kidney and spleen. β peptide deposits, however, are usually found only in the brain, although Joachim et al., *Nature* 341:226–228 (1989) have reported S peptide deposits outside the brain in the skin, intestine, and subcutaneous tissues of most AD patients.

The larger alternate forms of APP (APP751, APP770) consist of all of APP695 plus one or two additional domains. APP751 consists of all of APP695 plus an additional 56 amino acids which has homology to the Kunitz family of serine protease inhibitors (KP1) (Tanzi et al., 1988; Weidemann, et al., *Cell* 57:115–126 (1989); Kitaguchi, et al., *Nature* 331:530–532 (1988); Tanzi et al., *Nature* 329, 156 (1987). APP770 contains APP751 and an additional 19 amino acid domain homologous to the neuron cell surface antigen OX-2 (Weidemann, et al., *Cell* 57:115–126 (1989); Kitaguchi et al., 1988). APP is post-translationally modified by the removal of the leader sequence and by the addition of sulfate and sugar groups.

Van Broeckhaven, et al., *Science* 248:1120–1122 (1990) have demonstrated that the APP gene is tightly linked to hereditary cerebral hemorrhage with amyloidosis (HCHWA-D) in two Dutch families. This was confirmed by the finding of a point mutation in the APP coding region in two Dutch patients (Levy et al., *Science* 248:1124–1128 (1990). The mutation substituted a glutamine for glutamic acid at position 22 of the β peptide (position 618 of APP695). In addition, certain families are genetically predisposed to Alzheimer's disease, a condition referred to as familial Alzheimer's disease (FAD), through mutations resulting in an amino acid replacement at position 717 of the full length protein (Goate, et al., (1991); Murrell et al., 1991; Chartier-Harlin et al., 1991). These mutations co-segregate with the disease within the families and are absent in families with late-onset AD.

There are no proven animal models to study AD, although aging nonhuman primates seem to develop amyloid plaques of β peptide in brain parenchyma and in the walls of some meningeal and cortical vessels. Although aged primates and canines can serve as animal models, they are expensive to maintain and need lengthy study periods. There are no spontaneous animal mutations with sufficient similarities to AD to be useful as experimental models. Various models have been proposed in which some AD-like symptoms may be induced by electrolysis, transplantation of AD brain samples, aluminum chloride, kainic acid or choline analogs (Kisner, et al., *Neurobiol. Aging* 7;287–292 (1986); Mistry, J. S., et al., *J Med Chem* 29;337–343 (1986)). Flood, et al. (*Proc. Natl. Acad. Sci.* 88:3363 –3366 (1986), reported amnestic effects in mice of four synthetic peptides homologous to the β peptide. Because none of these share with AD either common symptoms, biochemistry or pathogenesis, they are not likely to yield much useful information on etiology or treatment.

Transgenic mice with the human APP promoter linked to *E. coli* β-galactosidase (Wirak, D. O., et al., *The EMBO J* 10;289–296 (1991)) as well as transgenic mice expressing the human APP751 cDNA (Quon, D, et al. *Nature* 352, 239–241 (1991)) or subfragment of the cDNA including the β peptide (Wirak, D. O., et al., *Science* 253, 323–325 (1991); Sandhu, F. A., et al., *J. Biol. Chem.* 266, 21331–21334 (1991); Kawabata, S. *Nature* 354, 476–478 (1991)) have been produced. Results obtained in the different studies appear to depend upon the source of promoter and the protein coding sequence used. For example, Wirak, et al. (1991) found that in transgenic mice expressing a form of the β peptide, intracellular deposits of "amyloid-like" material, reactive with antibodies prepared against APP were observed but did not find other histopathological disease symptoms. The intracellular nature of the antibody-reactive material and the lack of other symptoms suggest that this particular transgenic animal is not a faithful model system for Alzheimer's disease. Kawabata et al. (1991) report the production of amyloid plaques, neurofibrillary tangles, and neuronal cell death in their transgenic animals. In each of these studies, the same peptide fragment, the β peptide plus the 56 remaining C terminal amino acids of APP, was expressed. Wirak et al. (1991) used the human APP promoter while Kawabata, et al. (1991) used the human thy-1 promoter. In transgenic mice expressing the APP751 cDNA from the neuron-specific enolase promoter of Quon, D., et al., Nature 352, 239–241 (1991), extracellular deposits of material reactive with antibody prepared against APP were observed. What was not shown was whether the deposits contained full-length APP751 or β peptide or both, thus precluding any correlation of the deposits with those present in Alzheimer's disease. Quon et al. (1991) also state that the protein encoded by the APP695 cDNA expressed from the neuron-specific enolase promoter, does not form extracellular immunoreactive deposits. These results raise the possibility that although the β peptide is included within the APP695 precursor, use of the neuron-specific enolase promoter in conjunction with the APP695 cDNA may not present an effective Alzheimer's disease model. Furthermore, the presence of APP immunoreactive deposits is not correlated with the age or gene dosage in their particular transgenic model.

Alzheimer's disease is a complex syndrome involving pathological and behavioral aspects. A useful disease model should take these complexities into account. There are multiple proteins expressed from the gene with certain forms predominating in a given tissue. In the brain, the 695 form is predominant, but the mRNAs for additional forms are also present (Golde et al., Neuron 4; 253–267 (1990)). It is not known whether the ratio of the different forms changes with the age of the individual. The various protein forms result from alternative splicing such that the KI domain and/or the OX-2 domain may or may not be present in the mature protein. Moreover, the β-peptide results from post-translational processing of the precursor protein. This process can change in time as an individual ages, and can be affected by mutations not directly affecting the structure of the β-peptide:for example, the familial Alzheimer's disease (FAD) mutations at amino acid position 717 in the full length protein (Groate, et al., 1991; Murrell, et al., 1991; Chartier-Harlin, et al., 1991). Given these considerations, the production of universal animal models for Alzheimer's disease necessitates the construction of animal models that take into account the effects of known mutations on the phenotype resulting from the expression of these forms, and the possibility of the ratio of the different forms changing during the lifetime of the animal.

It is therefore an object of the present invention to provide an animal model for Alzheimer's disease that is constructed using transgenic technology.

It is a further object of the present invention to provide transgenic animals that accurately reflect the expression of different forms of the amyloid precursor protein.

It is a still further object of the present invention to provide transgenic animals characterized by certain genetic abnormalities in the expression of the amyloid precursor protein.

SUMMARY OF THE INVENTION

The construction of transgenic animal models for testing potential treatments for Alzheimer's disease is described. The models are characterized by a greater similarity to the conditions existing in naturally occurring Alzheimer's disease, based on the ability to control expression of one or more of the three forms of the β-amyloid precursor protein (APP), APP695, APP751, and APP770, or subfragments thereof, as well as various point mutations based on naturally occurring mutations, such as the FAD mutations at amino acid 717, and predicted mutations in the APP gene. The APP gene constructs are prepared using the naturally occurring APP promoter of human, mouse, or rat origin, as well as inducible promoters such as the mouse metallothionine promoter, which can be regulated by addition of heavy metals such as zinc to the animal's water or diet. Neuron-specific expression of constructs is achieved by using the rat neuron specific enolase promoter.

The constructs are introduced into animal embryos using standard techniques such as microinjection or embryonic stem cells. Cell culture based models can also be prepared by two methods. Cell cultures can be isolated from the transgenic animals or prepared from established cell cultures using the same constructs with standard cell transfection techniques.

The specific constructs that are described employ the following protein coding sequences: the APP770 cDNA; the APP770 cDNA bearing a mutation at amino acid 717; the APP751 cDNA containing the KI protease inhibitor domain without the OX2 domain in the construct; the APP751 cDNA and bearing a mutation at amino acid 717; the APP695 cDNA; the APP695 cDNA bearing a mutation at amino acid 717; the APP leader sequence followed by the β peptide region plus the remaining carboxy terminal 56 amino acids of APP; the APP leader sequence followed by the β peptide region plus the remaining carboxy terminal 56 amino acids with the addition of a mutation at amino acid 717; the APP leader sequence followed by the β peptide region; the β peptide region plus the remaining carboxy terminal 56 amino acids of APP; the β peptide region plus the remaining carboxy terminal 56 amino acids of APP with the addition of a mutation at amino acid 717; a combination genomic-cDNA APP gene construct; and a combination genomic-cDNA APP gene construct, with the addition of a mutation at amino acid 717, operably linked to promoters selected from the following: the human APP gene promoter, mouse APP gene promoter, rat APP gene promoter, metallothionine gene promoter, rat neuron specific enolase gene promoter, human β actin gene promoter, human platelet derived growth factor B (PDGF-B) chain gene promoter, rat sodium channel gene promoter, mouse myelin basic protein gene promoter, human copper-zinc superoxide dismutase gene promoter, and mammalian POU-domain regulatory gene promoter. Additional constructs include a human yeast artificial chromosome construct controlled by the human APP promoter; a human yeast artificial chromosome construct controlled by the human APP promoter with the addition of a mutation at amino acid 717; the endogenous mouse or rat APP gene modified through the process of homologous recombination between the APP gene in a mouse or rat embryonic stem (ES) cell and a vector carrying the human APP cDNA of the wild-type such that sequences in the resident rodent chromosomal APP gene beyond the recombination point (the preferred site for recombination is within APP exon 9) are replaced by the analogous human sequences; the endogenous mouse or rat APP gene modified through the process of homologous recombination between the APP gene in a mouse or rat ES cell and a vector carrying the human APP cDNA bearing a mutation at amino acid position 717 such that sequences in the resident rodent chromosomal APP gene beyond the recombination point (the preferred site for recombination is within APP exon 9) are replaced by the analogous human sequences bearing a mutation at amino acid 717. These constructs can be introduced into the transgenic animals and then combined by mating of animals expressing the different constructs.

The transgenic animals, or animal cells, are used to screen for compounds altering the pathological course of Alzheimer's Disease as measured by their effect on the amount and histopathology of APP and β peptide in the animals, as well as by behavioral alterations.

BRIEF DESCRIPTION OF THE DRAWINGS

The boxed portions of the drawings indicate the amino acid coding portions of the constructs. Filled portions indicate the various domains of the protein as indicated in the Figure Legend. Lines indicate sequences in the clones that are 5' or 3' untranslated sequences, flanking genomic sequences, or introns. The break in the line to the left of the constructs in FIGS. 7 and 8 indicates the presence of a long DNA sequence.

FIG. 1a is a schematic of the APP 770 cDNA coding sequence.

FIG. 1b is a schematic of the APP770 cDNA coding sequence bearing a mutation at position 717.

FIG. 2a is a schematic of the APP751 cDNA coding sequence.

FIG. 2b is a schematic of the APP751 cDNA coding sequence bearing a mutation at position 717.

FIG. 3a is a schematic of the APP695 coding sequence.

FIG. 3b is a schematic of the APP695 cDNA coding sequence bearing a mutation at position 717.

FIG. 4a is a schematic of a coding sequence for the carboxy terminal portion of APP.

FIG. 4b is a schematic of a coding sequence for the carboxy terminal portion of APP bearing a mutation at position 717.

FIG. 5 is a schematic of a coding sequence for the β peptide portion of APP.

FIG. 6a is a schematic of a combination genomic/cDNA coding sequence allowing alternative splicing of the KI and OX2 exons.

FIG. 6b is a schematic of a combination genomic/cDNA coding sequence bearing a mutation at position 717 and allowing alternative splicing of the KI and OX2 exons.

FIG. 7a is a schematic of a human APP YAC coding sequence.

FIG. 7b is a schematic of a human APP YAC coding sequence bearing a mutation at position 717.

FIGS. 8a and 8b are a schematic of genetic alteration of the mouse APP gene by homologous recombination between the mouse APP gene in a mouse ES cell and a vector carrying the human APP cDNA (either of the wild-type (FIG. 8a) or FAD mutant form) (FIG. 8b) directed to the exon 9 portion of the gene. As a result of this recombination event, sequences in the resident mouse chromosomal APP gene beyond the recombination point in exon 9 are replaced by the analogous human sequences.

DETAILED DESCRIPTION OF THE INVENTION

The constructs and transgenic animals and animal cells are prepared using the methods and materials described below.

Sources of materials

Restriction endonucleases are obtained from conventional commercial sources such as New England Biolabs (Beverly, Mass.), Promega Biological Research Products (Madison, Wis.), and Stratagene (LaJolla Calif.), etc. Radioactive materials are obtained from conventional commercial sources such as Dupont/NEN or Amersham. Custom-designed oligonucleotides for site-directed mutagenesis are available from any of several commercial providers of such materials such as Bio-Synthesis Inc., Lewisville, Tex. Kits for carrying out site-directed mutagenesis are available from commercial suppliers such as Promega Biological Research Products, Stratagene, etc. Clones of cDNA including the APP695, APP751, and APP770 forms of APP mRNA were obtained directly from Dr. Dmitry Goldgaber, NIH. Libraries of DNA are available from commercial providers such as Stratagene, La Jolla, Calif., or Clontech, Palo Alto, Calif.

PC12 and 3T3 cells were obtained from ATCC (#CRL1721 and #CCL92 respectively). An additional PC12 cell line was obtained from Dr. Charles Marotta of Harvard Medical School, Mass. General Hospital, and McLean Hospital. Standard cell culture media appropriate to the cell line are obtained from conventional commercial sources such as Gibco/BRL. Murine stem cells, strain D3, were obtained from Dr. Rolf Kemler (Doetschman, et al., *J. Embryol. Exp. Morphol.* 87, 27 (1985)). Lipofectin for DNA transfection and the drug G418 for selection of stable transformants are available from Gibco/BRL.

Isolation of the human APP promoter

A cosmid library, constructed from human placental DNA in the pWE15 cosmid vector, was screened by hybridization with a 32p-labeled probe prepared by nick-translation (Maniatis, et al. *Molecular Cloning: a laboratory manual* (Cold Spring Harbor Laboratory, Cold Spring Harbor, N.Y. 1989)) of the APP770 cDNA clone. Clones that hybridized with the probe were picked, purified, and characterized by restriction mapping, hybridization, and DNA sequencing. From one such clone containing a long 5' flanking region, a NotI to NruI restriction DNA fragment of approximately 25 kb was isolated. This fragment terminates 2 nucleotides before the initiator methionine codon of the Alzheimer's protein-coding region. This fragment, or a subfragment thereof, is the source of the human APP promoter for the constructs described herein. Analogous DNA fragments isolated using the same methods from mouse or rat genomic libraries are the source of mouse or rat promoters.

Definition of APP cDNA clones

The cDNA clone APP-695 is of the form of cDNA described by Kang, et al., *Nature* 325:733–735 ((1987), and represents the most predominant form of Alzheimer's protein in the brain. The cDNA clone APP-751 is of the form described by Ponte, P, *Nature* 331, 525–527 (1988). The cDNA clone APP-770 is of the form described by Kitaguchi, et al. *Nature* 331:530–532 (1988). This form contains an insert of 225 nucleotides relative to the 695 form. The 225 nucleotide insert encodes for the KI domain as well as the OX-2 domain.

Definition of the APP genomic locus

Characterization of phage and cosmid clones of human genomic DNA clones listed in the table below originally established a minimum size of at least 100 kb for the Alzheimer's gene. There are a total of 18 exons in the APP gene (Lemaire et al., *Nucl. Acid Res*, 17;517–522, 1989; Yoshikai et al., 1990). These results taken together indicate that the minimum size of the Alzheimer's gene is 175 kb.

I. Table of Alzheimer's Cosmid and Lambda Clones

| Library | Name of Clone | Insert Size (Kb) | Assigned APP Region |
|---|---|---|---|
| Cosmid | 1 GPAPP47A | 35 | 25 Kb promoter & 9 Kb intron 1 |
|  | 2 GPAAP36A | 35 | 12 Kb promoter & 22 Kb intron 1 |
|  | 3 GAPP30A | 30–35 | 5' coding region |
|  | 4 GAPP43A | 30–35 | exons 9, 10 and 11 |
| Lambda | 1 GAPP6A | 12 | exon 6 |
|  | 2 GAPP6B | 18 | exons 4 and 5 |
|  | 3 GAPP20A | 20 | exon 6 |
|  | 4 GAPP20B | 17 | exons 4 and 5 |
|  | 5 GAPP28A | 18 | exons 4 and 5 |

I. Table of Alzheimer's Cosmid and Lambda Clones -continued

| Library | Name of Clone | Insert Size (Kb) | Assigned APP Region |
|---|---|---|---|
|  | 6 GAPP3A | 14 | exon 6 |
|  | 7 GAPP4A | 19 | exon 6 |
|  | 8 GAPP10A | 16 | exons 9, 10 and 11 |
|  | 9 GAPP16A | 21 | exon 6 |

Construction of Transgenes

The clones bearing various portions of the human APP gene sequence shown in FIGS. 1–5 are constructed in an analogous manner. First, the polyA addition signal from SV40 virus as a 253 base pair BclI to BamHI fragment (Reddy et al., *Science* 200;494–502 (1978) is cloned into a modified vector from the pUC series. Next, the cDNA coding sequences (770, 751, or 695) are inserted. Correct orientation and content of the fragments inserted is determined through restriction endonuclease mapping and limited sequencing.

The clones bearing various carboxy terminal portions of the human APP gene sequence shown in FIGS. 4 and 5 are constructed through several steps in addition to those indicated above. First, an APP770 cDNA clone is digested with Asp718 which cleaves after position 56 (numbering system of Kang et al., 1987). The resulting 5' extension is filled in using the Klenow enzyme (Maniatis et al., 1989) and ligated to a hexanucleotide of the following sequence: AGATCT, the recognition site for BglII. After cleavage with BglII, which also cuts after position 1769, and re-ligation, the translational reading frame of the protein is preserved. The truncated protein thus encoded contains the leader sequence, followed by approximately 6 amino acids that precede the β peptide, followed by the β peptide, and the 56 terminal amino acids of APP. The clone in FIG. 5 is created by the introduction through site directed mutagenesis of nucleotide 1913 in the clone of FIG. 4a (numbering system of Kang et al., 1987) to a T thus creating a termination codon directly following the last amino acid codon of the peptide. Each of the APP cDNA sequence clones shown in FIGS. 1–5 contains a single NruI site 2 nucleotides upstream from the initiator methionine codon that is used for attachment of the different promoters used to complete each construct.

Expression clones identical to these but bearing mutations at the amino acid 717 of the full length protein, the site of the FAD mutation, are also constructed. Mutations at amino acid 717 are created by site-directed mutagenesis (Vincent, et al., *Genes & Devel.* 3, 334–347 (1989)) and include mutations of the wild-type val codon to one of the following codons; ile, phe, gly, tyr, leu, ala, pro, trp, met, ser, thr, asn, gln.

The preferred method for construction of the combination cDNA/genomic expression clones in FIG. 6 is as follows. The TaqI site at position 860 (numbering system of Kang, et al., 1987) in an APP770 cDNA clone is converted to an XhoI site by site-directed mutagenesis. Cleavage of the resulting plasmid with XhoI cuts at the new XhoI site and a pre-existing site at 930, and releases the KI and OX-2 coding sequence.

The plasmid thus generated serves as the acceptor for the KI and OX-2 alternative splicing cassette. The alternative splicing cassette is created through a series of cloning steps. First, the TaqI site at position 860 (numbering system of Kang, et al., 1987) in the genomic clone containing exon 6 and adjacent downstream intron is converted to an XhoI site by site-directed mutagenesis. Cleavage of the resulting plasmid with XhoI cuts at the new XhoI site and an XhoI site within the adjacent intron. This fragment is cloned into the XhoI site in a plasmid vector. Second, the genomic clone containing exon 9 and adjacent upstream intron is cleaved with XhoI (position 930) and cloned into the XhoI site of a plasmid vector. These two junction exon/intron fragments are released from their respective plasmid backbones by cleavage with XhoI and either BamHI or BglII, and cloned into the XhoI site of a plasmid vector. The resulting XhoI fragment is cleaved with either BamHI or BglII and the genomic 6.6 kb BamHI segment (Kitaguchi et al., 1988) containing the KI and OX-2 coding region along with their flanking intron sequences are inserted. After cleavage with XhoI, this DNA segment is inserted into the XhoI site of the modified APP770 cDNA constructed above. These cloning steps generate a combination cDNA/genomic expression clone that allows cells in a transgenic animal to regulate the inclusion of the KI and OX-2 domains by a natural alternative splicing mechanism. An analogous gene bearing a mutation at amino acid 717 is constructed by using the mutated form of APP770 cDNA described above.

Activity of Gene Promoters

Different promoter sequences are used to control expression of APP coding sequences. The ability to regulate expression of the APP gene in transgenic animals is believed to be useful in evaluating the roles of the different APP gene products in AD. The ability to regulate expression of the APP gene in cultured cells is believed to be useful in evaluating expression and processing of the different APP gene products and may provide the basis for cell cultured drug screens.

The metallothionine (MT) promoter is well characterized, has been employed in transgenic animals, and its expression can be regulated through modulation of zinc and glucocorticoid hormone levels (Palmiter et al., Nature 300, 611–615 (1982)).

The human APP promoter is also characterized with regard to expression in the CNS (Wirak et al., 1991). It is believed that this promoter is useful for accurately reproducing temporal and spatial expression of human APP sequences in the CNS of transgenic rodents. In addition to the human APP promoter, the APP promoter from mouse and rat is used in conjunction with the various wild-type and mutant APP coding sequences. Although the human APP promoter has been shown to have activity in the appropriate regions of the brain of transgenic mice (Wirak et al., 1991), it is believed that the use of a mouse APP promoter in a transgenic mouse or a rat APP promoter in a transgenic rat will offer an even more precise pattern of expression in the CNS of transgenic animals.

As an alternative for the control of human APP expression in neurons, the rat neuron specific enolase gene promoter is used. This promoter has been shown to direct expression of coding sequences in neurons (Forss-Petter et al., Neuron 5;197–197 (1990)).

Other alternatives for use in controlling human APP expression in neurons include the human S actin gene promoter (Ray et al., Genes and Development 5:2265–2273 (1991)), the human platelet derived growth factor B (PDGF-B) chain gene promoter (Sasahara et al., Cell 64:217–227 (1991)), the rat sodium channel gene promoter (Maue et al., Neuron 4:223–231 (1990)), the human copper-zinc superoxide dismutase gene promoter (Ceballos-Picot et al., Brain Res. 552:198–214 (1991)), and promoters for members of the mammalian POU-domain regulatory gene family (Xi et al., Nature 340:35–42 (1989)). The POU-domain is the region of similarity between the four mammalian transcription factors Pit-1, Oct-1, Oct.2, and unc-86, and represents a portion of the DNA-binding domain. These promoters are known or believed to result in expression specifically within the neurons of transgenic animals.

Expression of human APP in non-neuronal brain cells can be directed by the promoter for mouse myelin basic protein (Readhead et al., Cell 48:703–712 (1987)).

Yeast Artificial Chromosomes

The constructs shown in FIG. 7 are constructed as follows. Large segments of human genomic DNA, when cloned into certain vectors, can be propagated as autonomously-replicating units in the yeast cell. Such vector-borne segments are referred to as yeast artificial chromosomes (YAC; Burke et al. Science 236, 806 (1987)). A human YAC library is commercially available (Clontech, Palo Alto, Calif.) with an average insert size of 250,000 base pairs (range of 180,000 to 500,000 base pairs). A YAC clone of the Alzheimer's gene can be directly isolated by screening the library with the human APP770 cDNA. The inclusion of all of the essential gene regions in the clone can be confirmed by PCR analysis.

The YAC-APP clone, shown in FIG. 7a, is established in embryonic stem (ES) cells by selecting for neomycin resistance encoded by the YAC vector. ES cells bearing the YAC-APP clone are used to produce transgenic mice by established methods described below under "Transgenic Mice" and "Embryonic Stem Cell Methods". The YAC-APP gene bearing a mutation at amino acid 717 (FIG. 7b) is produced through the generation of a YAC library using genomic DNA from a person affected by a mutation at amino acid 717. The clone is identified and established in ES cells as described above.

Genetic Alteration of the Mouse APP Gene

The nucleotide sequence homology between the human and murine Alzheimer's protein genes is approximately 85%. Within the peptide-coding region, there are three amino acid differences between the two sequences. The val residue that is mutated at amino acid 717 is conserved between mouse, rat, and man. Wild-type rodents do not develop Alzheimer's disease nor do they develop deposits or plaques in their CNS analogous to those present in human Alzheimer's patients. Therefore, it is possible that the human but not the rodent form of B peptide is capable of causing disease. Homologous recombination (Capecchi, MR Science 244, 1288–1292 (1989)) can be used to convert the mouse Alzheimer's gens in situ to a gens encoding the human B peptide. This recombination is directed to a site downstream from the KI and OX-2 domains, for example, within exon 9, so that the natural alternative splicing mechanisms appropriate to all cells within-the transgenic animal can be employed in expressing the final gene product.

Both wild-type (FIG. 8, schematic "a") and mutant (FIG. 8, schematic "b") forms of human cDNA are used to produce transgenic models expressing either the wild-type or mutant forms of APP. The recombination vector is constructed from a human APP cDNA (695 or 770 form), either wild-type or mutant at amino acid 717. Cleavage of the recombination vector, for example, at the XhoI site within exon 9, promotes homologous recombination within the directly adjacent sequences (Capecchi, 1989). The endogenous APP gens resulting from this event is normal up to the point of recombination, within exon 9 in this example, and consists of the human cDNA sequence thereafter.

Mutant Forms of APP Proteins

Expression clones identical to these but bearing mutations at the amino acid 717 of the full length protein, the site of FAD mutations, are also constructed. Mutations at amino acid 717 are created by site-directed mutagenesis (Vincent, et al., 1989) and include mutations of the wild-type val codon to one of the following codons; ils, phe, gly, tyr, leu, ala, pro, trp, met, ser, thr, ash, gln. Mutations of val-717 to ils, phe, and gly, have been described (Goate et al., 1991; Murrell, et al., 1991; Chartier-harlin et al., 1991). None of these naturally-occurring mutations are charged or bulky amino acids. Therefore it is believed that replacement of val-717 with the other amino acids listed may also promote the FAD syndrome and have properties that are useful for animal AD models.

Preparation of Constructs for Transfections and MicroInjections

DNA clones for microinjection are cleaved with appropriate enzymes, such as Sal1, Not1, etc., and the DNA fragments electrophoresed on 1% agarose gels in TBE buffer (Maniatis et al., 1989). The DNA bands are visualized by staining with ethidium bromide, excised, and placed in dialysis bags containing 0.3M sodium acetate, pH 7.0. DNA is electroeluted into the dialysis bags, extracted with phenol-chloroform (1:1), and precipitated by two volumes of ethanol. The DNA is redissolved in 1 ml of low salt buffer (0.2M NaCl, 20 mM Tris™, pH 7.4, and 1 mM EDTA) and purified on an Elutip-D™ column. The column is first primed with 3 ml of high salt buffer (1M NaCl, 20 mMTris™, pH 7.4, and 1 mM EDTA) followed by washing with 5 ml of low salt buffer. The DNA solutions are passed through the column for three times to bind DNA to the column matrix. After one wash with 3 ml of low salt buffer, the DNA is eluted with 0.4 ml of high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris™, pH 7.4 and 0.1 mMEDTA. Other methods for purification of DNA for microinjection are also described in Hogan, et al., *Manipulating the mouse embryo* (Cold Spring Harbor Laboratory, Cold Spring Harbor, N.Y. (1986), in Palmiter, et al., *Nature* 300, 611 (1982), in "The Qiagenologist, Application Protocols", 3rd edition, published by Qiagen, Inc., Chatsworth, Calif., and in Maniatis, et al., *Molecular Cloning: a laboratory manual* (Cold Spring Harbor Laboratory, Cold Spring Harbor, N.Y. 1989).

Construction of Transgenic Animals

Animal Sources

Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Swiss Webster female mice are preferred for embryo retrieval and transfer. B6D2F$_1$ males can be used for mating and vasectomized Swiss Webster studs can be used to stimulate pseudopregnancy. Vasectomized mice and rats can be obtained from the supplier.

Microinjection Procedures

The procedures for manipulation of the rodent embryo and for microinjection of DNA are described in detail in Hogan et al. *Manipulating the mouse embryo*, Cold Spring Harbor Laboratory, Cold Spring harbor, N.Y. (1986), the teachings of which are incorporated herein.

Transgenic Mice

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10–12 embryos). The pipet tip is inserted into the infundibulum and the embryos transferred. After the transfer, the incision is closed by two sutures.

Transgenic Rats

The procedure for generating transgenic rats is similar to that of mice (Hammer et al., *Cell* 63;1099–112 (1990)). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPBS (Dulbecco's phosphate buffered saline) with 0.5% BSA and the embryos collected. Cumulus cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10–12 embryos are transferred into each rat oviduct through the infundibulum. The incision is then closed with sutures, and the foster mothers are housed singly.

Embryonic Stem (ES) Cell Methods

Introduction of cDNA into ES cells

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987), the teachings of which are incorporated herein. Selection of the desired clone of transgene-containing ES cells is accomplished through one of several means. In cases involving random gene integration, an APP clone is co-precipitated with a gene encoding neomycin resistance. Transfection is carried out by one of several methods described in detail in Lovell-Badge, in *Teratocarcinomas and embryonic stem cells, a practical approach*, ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, $0.5 \times 10^6$ ES cells are plated into tissue culture dishes and transfected with a mixture of the linearized APP clone and 1 mg of pSV2neo DNA (Southern and Berg, *J. Mol. Appl. Gen.* 1:327-341 (1982)) precipitated in the presence of 50 mg lipofectin in a final volume of 100 μl. The cells are fed with selection medium containing 10% fetal bovine serum in DMEM supplemented with G418 (between 200 and 500 μg/ml). Colonies of cells resistant to G418 are isolated using cloning rings and expanded. DNA is extracted from drug resistant clones and Southern blotting experiments using an APP770 cDNA probe are used to identify those clones carrying the APP sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150-153 (1989). DNA introduction byelectroporation is less efficient and requires a selection step. Methods for positive selection of the recombination event (i.e., neo resistance) and dual positive-negative selection (i.e., neo resistance and gancyclovir resistance) and the subsequent identification of the desired clones by PCR have been described by Joyner et al., *Nature* 338, 153-156 (1989) and Capecchi, (1989), the teachings of which are incorporated herein.

Embryo Recovery and ES cell Injection

Naturally cycling or superovulated female mice mated with males are used to harvest embryos for the implantation of ES cells. It is desirable to use the C57B strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10-20 ES cells are injected into blastocysts using a glass microneedle with an internal diameter of approximately 20 μm.

Transfer of Embryos to Pseudopregnant Females

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

Identification of Transgenic Mice and Rats

Tail samples (1-2 cm) are removed from three week old animals. DNA is prepared and analyzed by both Southern blot and PCR to detect transgenic founder ($F_0$) animals and their progeny ($F_1$ and $F_2$).

Pathological Studies

The various $F_0$, $F_1$, and $F_2$ animals that carry the microinjected transgene are sacrificed by $CO_2$ asphyxiation and analyzed by immunohistology for neuritic plaques and neurofibrillary tangles (NFTs) in the brain. Brains of mice and rats from each transgenic line are fixed in 4% paraformaldehyde and sectioned on a cryostat. Sections are stained with antibodies reactive with the APP and/or the β peptide. Secondary antibodies conjugated with fluorescein, rhodamine, horse radish peroxidase, or alkaline phosphatase are used to detect the primary antibody. These experiments permit identification of amyloid plaques and the regionalization of these plaques to specific areas of the brain. Plaques ranging in size from 9 to 50 μm characteristically occur in the brains of AD patients in the cerebral cortex, but also may be observed in deeper grey matter including the amygdaloid nucleus, corpus striatum and diencephalon. Sections are also stained with other antibodies diagnostic of Alzheimer's plaques, recognizing antigens such as Alz-50, tau, A2B5, neurofilaments, neuron-specific enolase, and others that are characteristic of Alzheimer's plaques (Wolozin, et al., *Science* 232, 648 (1986); Hardy and Allsop, *Trends in Pharm. Sci.* 12, 383-388 (1991); Selkoe, *Ann. Rev. Neurosci.* 12, 463-490 (1989); Arai et al., *Proc. Natl. Acad. Sci. USA* 87, 2249-2253 (1990); Majocha et al., *Amer. Assoc. Neuropathology* Abs; 99,22 (1988); Masters et al., *Proc. Natl. Acad. Sci.* 82,4245-4249; Majocha et al., *Can J Biochem Cell Biol* 63;577-584 (1985)). Staining with thioflavins and congo red is also carried out to analyze co-localization of β peptide deposits within neuritic plaques and NFTs.

Analysis of APP and β Peptide Expression mRNA: mRNA is isolated by the acid guanidinium thiocyanate-phenol:chloroform extraction method (Chomczynski and Sacchi, *Anal Biochem* 162,156-159 (1987)) from cell lines and tissues of transgenic animals to determine expression levels by Northern blots.

Protein: APP and β peptide are detected by using polyclonal and monoclonal antibodies that are specific to the extra-cytoplasmic domain, β peptide region, and C-terminus.

Western Blot Analysis: Protein fractions are isolated from tissue homogenates and cell lysates and subjected to Western blot analysis as described by Harlow et al., *Antibodies: A*

*laboratory manual,* (Cold Spring Harbor, N.Y., 1988); Brown et al., *J. Neurochem.* 40;299–308 (1983); and Tate-Ostroff et al, *Proc Natl Acad Sci* 86;745–749 (1989)). Only a brief description is given below.

The protein fractions are denatured in Laemmli sample buffer and electrophoresed on SDS-Polyacrylamide gels. The proteins are be then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of APP proteins.

Pathological and Behavioral Studies

Pathological Studies

Immunohistology and thioflavin S staining are conducted as described elsewhere herein.

In situ Hybridizations: Radioactive or enzymatically labeled probes are used to detect mRNA in situ. The probes are degraded approximately to 100 nucleotides in length for better penetration of cells. The procedure of Chou et al. *J. Psych. Res.* 24,27–50 (1990) for fixed and paraffin embedded samples is briefly described below although similar procedures can be employed with samples sectioned as frozen material. Paraffin slides for in situ hybridization are dewaxed in xylene and rehydrated in a graded series of ethanols and finally rinsed in phosphate buffered saline (PBS). The sections are post-fixed in fresh 4% paraformaldehyde. The slides are washed with PBS twice for 5 minutes to remove paraformaldehyde. Then the sections are permeabilized by treatment with a 20 µg/ml proteinase K solution. The sections are re-fixed in 4% parformaldehyde, and basic molecules that could give rise to background probe binding are acetylated in a 0.1M triethanolamine, 0.3M acetic anhydride solution for 10 minutes. The slides are washed in PBS, then dehydrated in a graded series of ethanols and air dried. Sections are hybridized with antisense probe, using sense probe as a control. After appropriate washing, bound radioactive probes are detected by autoradiography or enzymatically labeled probes are detected through reaction with the appropriate chromogenic substrates.

Behavioral Studies

Behavioral tests designed to assess learning and memory deficits are employed. An example of such as test is the Morris Water maze (Morris, *Learn Motivat.* 12;239–260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues.

The procedures applied to test transgenic mice is similar for transgenic rats.

Screening of Compounds for Treatment of Alzheimer's Disease

The transgenic animals and animal cells are used to screen compounds for a potential effect in the treatment of Alzheimer's disease using standard methodology. The compound is administered to the animals or introduced into the culture media over a period of time and in various dosages, then the animals or animal cells examined for alterations in APP expression, histopathology, and/or behavior using the procedures described above.

Example 1: Expression of pMTAPP-1 in NIH3T3 and PC12 Cells

The clone, pMTAPP-1 is an example of the expression vector shown in FIG. 1a where the promoter used is the metallothionine promoter. Stable cell lines were derived by transfecting NIH3T3 and PC12 cell lines (ATCC #CCL92 and CRL1721). $0.5 \times 10^6$ of NIH3T3 or PC12 cells were plated into 100 mm dishes and transfected with a mixture of 5 mg of the SalI fragment and 1 mg of pSV2neo DNA (46) precipitated in the presence of 50 mg lipofectin (Gibco, BRL) in a final volume of 100 µl. Polylysine-coated plates were used for PC12 cells, which normally do not adhere well to tissue culture dishes. The cells were fed with selection medium containing 10% fetal bovine serum in DMEM or RPMI and supplemented with G418. Five hundred mg/ml (biological weight) and 250 mg/ml of G418 were used to select colonies form NIH3T3 and PC12 cells, respectively. Fifteen days after transfection, colonies of cells resistant to G418 were isolated by cloning rings and expanded in T flasks. The presence of APP cDNA in the cells was detected by PCR, using the procedure of Mullis and Faloona, *Methods Enzymol.* 155;335–350 (1987), the teachings of which are incorporated herein.

Expression of APP in 25 colonies from each cell line was analyzed by immunostaining (Majocha etal., 1988). Cells were grown to subconfluence and fixed in a solution containing 4% paraformaldehyde, 0.12M NaCl, and 20 mm $Na_3PO_4$, pH 7.0. They were incubated overnight with a primary monoclonal antibody against a synthetic β peptide sequence (Masters et al., 1985) provided by Dr. Ronald Majocha, Mass. General Hospital, Boston, Mass., followed by a generalized anti-mouse antibody conjugated to biotin (Jackson ImmunoResearch Labs, Pa.). Immunostaining was then performed by adding avidin-horseradish peroxidase (HRP) (Vector Labs, Burlingame, Calif.) and diaminobenzidine as the chromogen (Majocha et al., 1985). The results indicated that the pMTAPP-1 vector was expressing APP in both NIH3T3 and PC12 cells.

Example 2: Expression of pEAPP-1 in PC12 Cells pEAPP-1 is an example of the 25 kb human APP gens promoter linked to and controlling expression of a human APP770 cDNA like the construct in FIG. 1A. DNA from this construct was transfected into PC12 cells as described above. Certain clone of pEAPP-1 transfected cells exhibited a differentiation phenotype morphologically similar to that exhibited by PC12 cells treated with nerve growth factor (NGF). PC12 cells normally are fairly round and flat cells. Those transfected with pEAPP-1 have cytoplasmic extensions resembling neurites. PC12 cells treated with NGF extend very long neuritic extensions. Thirteen PC12 cell clones transfected with pEAPP-1 were selected and propagated. Eight of these cell clones exhibited the spontaneous differentiation phenotype With clones 1-8, 1-1, and 1-4 exhibiting the strongest phenotypes. Staining of pEAPP-1 transfected PC12 cells with antibody against the β peptide as described. above indicated that those cells exhibiting the differentiation were also expressing APP. Because PC12 cells transfected with the pMTAPP1 clone did not exhibit this phenotype even though the APP770 cDNA is expressed, these results suggest that expression of APP770 from the human promoter has novel properties regarding the physiology of the cell.

Example 3: Expression of pMTA4 in PC12 Cells pMTA4 is an example of the type of construct shown in FIG. 4A where the promoter used is the metallothionine promoter. The protein encoded by this construct differs slightly from that depicted in FIG. 4. An APP770 cDNA clone was digested with Asp718 which cleaves after position 56 (number system of Kang, et al., 1987). The resulting 5' extension was filled in using the Klenow enzyme (Maniatis). The same DNA preparation was also cleaved with EcoRI which also cuts after position 1795 and the resulting 5' extension was filled in using the Klenow enzyme (Maniatis). Self-ligation of this molecule results in an expression clone in which the truncated protein thus encoded contains the leader sequence, followed by a shortened version of the β peptide starting with the sequence phe-arg-val-gly-ser-of the β peptide followedby the 56 terminal amino acids of APP. DNA from this construct was transfected into PC12 cells as described above.

Example 4: Generation of Transgenic Mice expressing APP under the control of the MT-1 promoter.

Transgenic mice were made by microinjecting pMTAPP1 vector DNA into pronuclear embryos. pMTAPP1 is an example of the type of construct shown in FIG. 1a which is operably linked to the metallothionine promoter. The procedures for microinjection into mouse embryos are described in "Manipulating the mouse embryo" by B. Hogan et al. (1986). Only a brief description of the procedures is described below.

Mice were obtained from Taconic Laboratories (German Town, New York). Swiss Webster female mice were used for embryo retrieval and implantation. B6D2F$_1$ males were used for mating and vasectomized Swiss webster studs were used to simulate pseudopregnancy.

Embryo Recovery: Female mice, 4 to 8 weeks of age, were induced to superovulate with 5 IU of pregnant mare's serum gonadotropin (PMSG; Sigma) followed 48 hours later by 5 IU of human chorionic gonadotropin (hCG; Sigma). Females were placed with males immediately after hCG injection. Embryos were recovered from excised oviducts of mated females 21 hours after hCG in Dulbecco's phosphate buffered saline with 0.5% bovine serum albumin (BSA; Sigma). Surrounding cumulus cells were removed with hyaluronidase (1 mg/ml). Pronuclear embryos were then washed and placed in Earle's balanced salt solution containing 0.4% BSA (EBSS) in a 37.5° C. incubator with a humidified atmosphere at 7% $CO_2$, 5% $O_2$, and 88% $N_2$ until the time of injection.

Microinjection: Elutip-D™ purified SaiI DNA was dissolved in 5 mM Tris (pH 7.4) and 0.1 mM EDTA at 3 µg/ml concentration for microinjection. Microneedles and holding pipettes were pulled from Fisher coagulation tubes (Fisher) on a DKI model 720 pipette puller. Holding pipettes were then broken at approximately 70 µm (O.D.) and fire polished to an I.D. of about 30 ∞m on a Narishige microforge (model MF-83). Pipettes were mounted on Narishige micromanipulators which were attached to a Nikon Diaphot microscope. The air-filled injection pipette was filled with DNA solution through the tip after breaking the tip against the holding pipette. Embryos, in groups of 30 to 40, were placed in 100l drops of EBBS under paraffin oil for micromanipulation. An embryo was oriented and held with the holding pipette. The injection pipette was then inserted into the male pronucleus (usually the larger one). If the pipette did not break through the membrane immediately the stage was tapped to assist in penetration. The nucleus was then injected and the injection was monitored by swelling of the nucleus. Following injection, the group of embryos was placed in EBSS until transfer to recipient females.

Transfer: Randomly cycling adult female mice were paired with vasectomized Swiss Webster males. Recipient females were mated at the same time as donor females. At the time of transfer, the females were anesthetized with avertin. The oviducts were exposed by a single midline dorsal incision. An incision was then made through the body wall directly over the oviduct. The ovarian bursa was then torn with watch makers forceps. Embryos to be transferred were placed in DPBS and in the tip of a transfer pipet (about 10–12 embryos). The pipet tip was inserted into the infundibulum and embryos were transferred. After the transfer, the incision was closed by two sutures.

Analysis Of Mice For Transgene Integration: At three weeks of age tail samples about 1 cm long were excised for DNA analysis. The tail samples were digested by incubating with shaking overnight at 55° C. in the presence of 0.7 ml 5 mM Tris, pH 8.0, 100 mM EDTA, 0.5% SDS and 350 µg of proteinase K. The digested material was extracted once with an equal volume of phenol and once with an equal volume of phenol:chloroform (1:1 mixture). The supernatants were mixed with 70 µl 3M sodium acetate (pH 6.0) and the DNAs were precipitated by adding equal volume of 100% ethanol. The DNAs were spun down in a microfuge, washed once with 70% ethanol, dried and dissolved in 100 µl TE buffer (10 mMtris pH 8.0 and 1 mM EDTA).

10–20 µl of DNAs were restricted with BamH1, electrophoresed on 1% agarose gels, blotted onto nitrocellulose paper, and hybridizewith $^{32}$P-labeled APP cDNA fragment. Transgenic animals were identified by autoradiography of the hybridized nitrocellulose filters. The DNAs were also analyzed by PCR carried out by synthetic primers to generate an 800 bp fragment.

A total of 671 pronuclear embryos were microinjected out of which 73 live and 6 dead pups were born. DNA analysis identified 9 transgenic mice (5 females and 4 males) which were bred to generate $F_1$ and $F_2$ transgenics. These animals can be analyzed, for expression of mRNA and protein of APP in different tissues and for analysis of behavioral and pathological abnormalities as described above.

Modifications and variations of the making and testing of transgenic animal models for testing of Alzheimer's disease will be obvious to those skilled in the art from the foregoing detailed description. Such modifications and variations are intended to come within the scope of the following claims.

We claim:

1. A method for screening compounds for an effect on Alzheimer's disease comprising administering the compound to be tested to a transgenic mouse having integrated into the chromosome a nucleic acid construct, wherein the construct comprises a mammalian promoter operatively linked to a cDNA-genomic DNA hybrid sequence, wherein said hybrid sequence contains a cDNA sequence encoding APP770 or a cDNA encoding APP770 with a naturally occurring mutation, wherein a genomic APP DNA sequence consisting of exon 6 and an amount of the adjacent downstream intron sufficient for Splicing, the KI and OX-2 coding regions and an mount of each of their upstream and downstream introns sufficient for splicing, and exon 9 and an amount of the adjacent upstream intron sufficient for splicing is substituted into the cDNA sequence encoding APP770 or the cDNA sequence encoding APP770 with a naturally occurring mutation, and wherein the construct is transcribed and differentially spliced in the transgenic mouse to form mRNA which is translated into APP695, APP751 and APP770, and determining if there is altered expression or processing of APP, wherein the presence of altered expression or processing of APP is indicative of an effect of the compound on Alzheimer's disease.

2. The method of claim 1 wherein the construct includes a mutation at amino acid 717.

3. The method of claim 1 wherein the construct includes a promoter selected from the group consisting of the human AlP promoter, metallothionine promoter, rat neuron specific enolase promoter, and human platelet derived growth factor B chain promoter.

4. The method of claim 1 wherein the promoter is the human platelet derived growth factor B chain promoter.

5. The method of claim 1 further comprising determining if the brain histopathology, or the behavior of the transgenic mouse is altered after administration of the compound to the mouse.

6. The method of claim 1 wherein altered expression or processing of APP is determined by measuring the level of $\beta$ peptide produced by the transgenic mouse and comparing the measured level to the level of $\beta$ peptide produced by a transgenic mouse to which the compound has not been administered.

* * * * *